United States Patent
Kim

(10) Patent No.: US 9,455,065 B2
(45) Date of Patent: *Sep. 27, 2016

(54) NANO STRUCTURE INCLUDING DIELECTRIC PARTICLE SUPPORTER

(71) Applicant: SK INNOVATION CO., LTD., Seoul (KR)

(72) Inventor: Jun-Hyung Kim, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 87 days.

This patent is subject to a terminal disclaimer.

(21) Appl. No.: 14/312,453

(22) Filed: Jun. 23, 2014

(65) Prior Publication Data
US 2015/0179299 A1    Jun. 25, 2015

(30) Foreign Application Priority Data

Dec. 19, 2013  (KR) .................. 10-2013-0159743
Dec. 19, 2013  (KR) .................. 10-2013-0159752
Dec. 19, 2013  (KR) .................. 10-2013-0159766

(51) Int. Cl.
| | |
|---|---|
| *H01B 3/18* | (2006.01) |
| *C07F 7/10* | (2006.01) |
| *C07F 1/00* | (2006.01) |
| *B82Y 30/00* | (2011.01) |

(52) U.S. Cl.
CPC ............... *H01B 3/18* (2013.01); *B82Y 30/00* (2013.01); *C07F 1/005* (2013.01); *C07F 7/10* (2013.01); *Y10T 428/256* (2015.01); *Y10T 428/31663* (2015.04)

(58) Field of Classification Search
CPC ........... C07F 7/10; C07F 1/005; H01B 3/18; B82Y 30/00
USPC ................. 556/9, 12; 428/328, 447
See application file for complete search history.

(56) References Cited

U.S. PATENT DOCUMENTS

| | | |
|---|---|---|
| 2011/0059264 A1 | 3/2011 | Park et al. |
| 2012/0130053 A1 | 5/2012 | Lee et al. |
| 2015/0174607 A1* | 6/2015 | Kim ............... B05D 1/185 427/552 |
| 2015/0174855 A1* | 6/2015 | Kim ............... C23C 18/1882 428/323 |
| 2015/0175411 A1* | 6/2015 | Kim ............... B81C 1/00373 427/597 |
| 2015/0175633 A1* | 6/2015 | Kim ............... C07F 1/005 556/9 |

FOREIGN PATENT DOCUMENTS

| | | |
|---|---|---|
| JP | 2003-168606 | 6/2003 |
| WO | WO 2008/068873 | 6/2008 |
| WO | WO 2013/006207 | 1/2013 |

OTHER PUBLICATIONS

Westcott, S. L., et al., Formation and Adsorption of Clusters of Gold Nanoparticles Surfaces, Langmuir, Sep. 15, 1998, pp. 5396-5401, vol. 14, No. 19.

(Continued)

*Primary Examiner* — Porfirio Nazario Gonzalez
(74) *Attorney, Agent, or Firm* — IP & T Group LLP

(57) ABSTRACT

Provided are a nano structure, a fabrication method thereof, and an application device using the same. The nano structure includes a substrate; a dielectric particle supporter having a surface, wherein the dielectric particle supporter is formed over the substrate, and a linker bonded to the surface of the dielectric particle supporter; and a metallic nanoparticle bonded to the linker.

24 Claims, 6 Drawing Sheets

(56) References Cited

OTHER PUBLICATIONS

Hurst, K. M., et al., Self-Assembled Monolayer-Immobilized Gold Nanoparticles as Durable, Anti-Stiction Coatings for MEMS, Journal of Microelectromechanical Systems, Apr. 1, 2011, pp. 424-435, vol. 20, No. 2.

Extended European Search Report issued by the European Patent Office on May 19, 2015.

* cited by examiner

NANO STRUCTURE INCLUDING DIELECTRIC PARTICLE SUPPORTER

CROSS-REFERENCE TO RELATED APPLICATIONS

The present application claims priority of Korean Patent Application Nos. 10-2013-0159743, 10-2013-0159766, and 10-2013-0159752 filed on Dec. 19, 2013, which are incorporated herein by reference in their entirety.

BACKGROUND

1. Field

Various embodiments of the present disclosure relate to a nano structure including a dielectric particle supporter, a fabrication method thereof, and an application device thereof.

2. Description of the Related Art

Nano structures have characteristics such as the quantum confinement effect, the Hall-Petch effect, dropping melting point, resonance phenomenon, excellent carrier mobility and so forth in comparison with conventional bulk and thin firm-type structures. For this reason, the nano structure is being applied to chemical batteries, solar cells, semiconductor devices, chemical sensors, photoelectric devices and the like.

Nano structures are being fabricated in either a top-down method or a bottom-up method. The bottom-up method includes a vapor-liquid-solid growth method and a liquid growth method. The vapor-liquid-solid growth method is based on a catalytic reaction and includes methods such as the Thermal Chemical Vapor Deposition (thermal-CVD) method, the Metal-Organic Chemical Vapor Deposition (MOCVD) method, the Pulsed Laser Deposition (PLD) method, and the Atomic Layer Deposition (ALD) method. As for the liquid growth method, a self-assembly technology and a hydrothermal method are being suggested.

According to the conventional bottom-up method, nanoparticles are prepared in advance and then the nanoparticles are attached to a substrate having a modified surface. However, this method is limited because it has difficult in controlling the size of nanoparticles which results in deteriorated memory device reproducibility and reliability. In other words, with the method of fabricating a nano structure by simply attaching nanoparticles to a substrate, it is likely impossible to improve memory performance unless nanoparticle synthesis technology makes remarkable progress.

To overcome this limitation, nanoparticles may be prepared in a top-down method such as lithography. The use of the top-down method, however, requires a great deal of investment in equipment, because a high-end lithography facility is needed. Moreover, since the process is quite complicated, the ability to implement it in mass-production is limited. Also, although the etch process is performed using an electron beam, it is difficult to keep the nanoparticles size under a predetermined level.

SUMMARY

Various embodiments are directed to a nano structure that may be quickly mass-produced through a method that is commercially available and cost-effective, and a fabrication method thereof.

Also, various embodiments are directed to a nano structure having nanoparticles whose size may be controlled, and a fabrication method thereof.

Also, various embodiments are directed to a nano structure capable of securing operation stability, reproducibility, and reliability of an application device even when scaled.

Also, various embodiments are directed to a device including a nano structure having excellent operation stability, reproducibility, and reliability.

In an embodiment, a nano structure includes: a substrate; a dielectric particle supporter having a surface, wherein the dielectric particle supporter is formed over the substrate, and a linker bonded to the surface of the dielectric particle supporter; and a metallic nanoparticle bonded to the linker.

The metallic nanoparticle may be grown from a metal ion bonded to the linker.

The dielectric particle supporter may include at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, and a hafnium silicate.

The nano structure may further include: at least one between a dielectric organic material and an inorganic oxide that is bonded to a surface of the metallic nanoparticle.

The nano structure may further include: an organic surfactant of one or more kinds bonded to the metal ions or the nanoparticles which are being grown.

When a surfactant is not included, the metallic nanoparticles may have an average particle diameter of about 2.0 to 3.0 nm.

The organic surfactant may be a nitrogen-containing organic material or a sulfur-containing organic material, and the metallic nanoparticles may have an average particle diameter of about 1.3 nm to 1.9 nm.

The organic surfactant may include a first organic material and a second organic material of different kinds, and the first organic material may be a nitrogen-containing organic material or a sulfur-containing organic material, and the second organic material may foe a phase-transfer catalyst-based organic material. The metallic nanoparticles may have an average particle diameter of about 0.5 nm to 1.2 nm.

The linker may include an organic monomolecule bonded to a surface of the dielectric particle supporter.

The linker may include a first functional group bonded to a surface of the dielectric particle supporter, a second functional group bonded to the metal ions, and a chain group for connecting the first functional group and the second functional group to each other.

The linker may include one functional group selected from the group including an amine group, a carboxyl group and a thiol group as a functional group capable of being bonded to the metal ions.

The metallic nanoparticles may be selected from the group including a metal nanoparticle, a metal oxide nanoparticle, a metal nitride nanoparticle, a metal carbide nanoparticle, and an intermetallic compound nanoparticle.

The metallic nanoparticles may be arranged separately from one another and form a single mono-molecular layer.

A plurality of the dielectric particle supporters, each of which is bonded to the linkers, may be arranged over the substrate to form a supporter layer, which is a monomolecular supporter layer or a multimolecular supporter layer.

The nano structure may further include; a nanoparticle layer formed over the supporter layer, and the nanoparticle layer includes: a plurality of the metallic nanoparticles spaced apart from each other; and a dielectric material bonded to a surface of each metallic nanoparticle.

A plurality of the supporter layers and a plurality of the nanoparticle layers may be stacked alternately and repeatedly to form a vertical multi-stack structure.

The dielectric material may include at least one between a dielectric organic material and an inorganic oxide.

In another embodiment, a nano structure includes: a substrate; a plurality of dielectric particle supporters disposed over the substrate; a plurality of linkers formed on the dielectric particle supporters and suitable for coupling a plurality of metal ions with the dielectric particle supporters; and one or more metallic nanoparticles formed to the linkers.

Each of the linkers may includes one functional group selected from the group including an amine group, a carboxyl group, and a thiol group, as a functional group that is bonded to the metal ions.

The nano structure may further comprising; an organic surfactant of one or more kinds bonded to the metal ions or the nanoparticles.

The metallic nanoparticles may have an average diameter of 0.5 nm to 3.0 nm. The metallic nanoparticles may have a particle radius standard deviation of 20% or less.

DETAILED DESCRIPTION

Figure 1A:
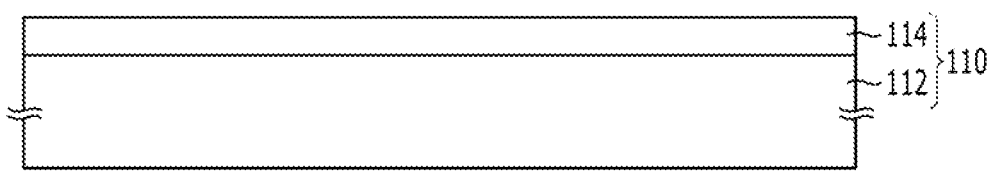
FIGS. 1A to 1F are cross-sectional views illustrating a nano structure and a method for fabricating the nano structure in accordance with a first embodiment of the present disclosure.

Hereinafter, a single electron transistor and a fabrication method thereof according to embodiments of the present disclosure will be described in detail with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the present disclosure to those skilled in the art. In addition, the drawings are not necessarily to scale and, in some instances, proportions may have been exaggerated in order to clearly illustrate features of the embodiments. Throughout the disclosure, reference numerals correspond to the like numbered parts in the various figures and embodiments of the present invention.

It should be understood that the meaning of "on" and "over" in the present disclosure should be interpreted in the broadest manner such that "on" means not only "directly on" but also "on" something with intermediate feature(s) or layer(s) therebetween, and that "over" means not only directly on but also on something with an intermediate feature(s) or layer(s) therebetween. It is also noted that in this specification, "connected/coupled" refers to one component not only directly coupling another component but also indirectly coupling another component through an intermediate component. In addition, a singular form may include a plural form, and vice versa, as long as it is not specifically mentioned.

Unless otherwise mentioned, all terms used herein, including technical or scientific terms, have the same meanings as understood by those skilled in the technical field to which the present disclosure pertains. In the following description, a detailed description of known functions and configurations will be omitted when it may obscure the subject matter of the present disclosure.

[Nano Structure and Fabrication Method Thereof in Accordance with a First Embodiment of the Present Invention]

FIGS. 1A to 1F are cross-sectional views illustrating a nano structure and a method for fabricating the nano structure in accordance with a first embodiment of the present disclosure.

Figure 1B:
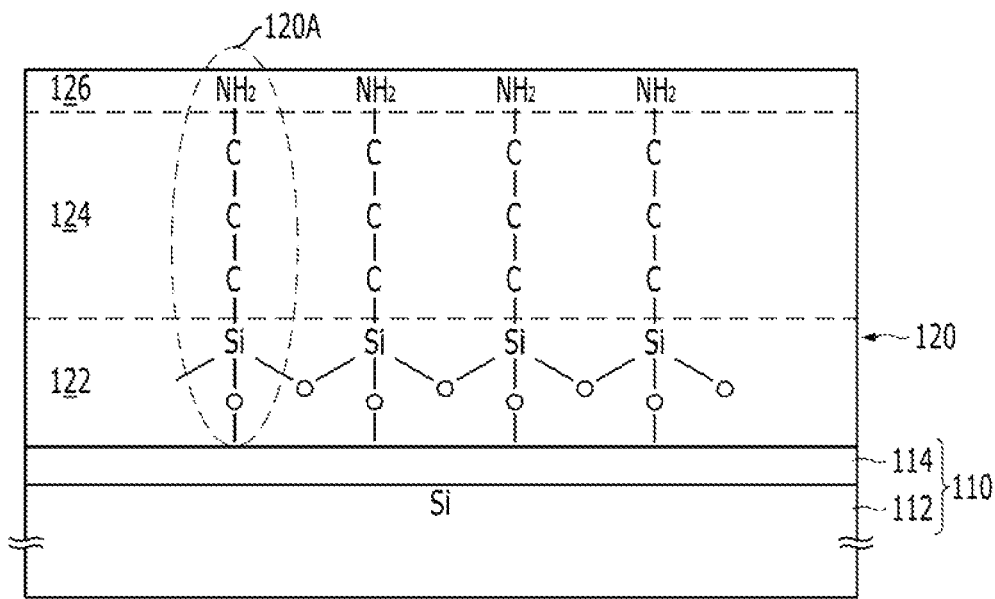
Figure 1C:
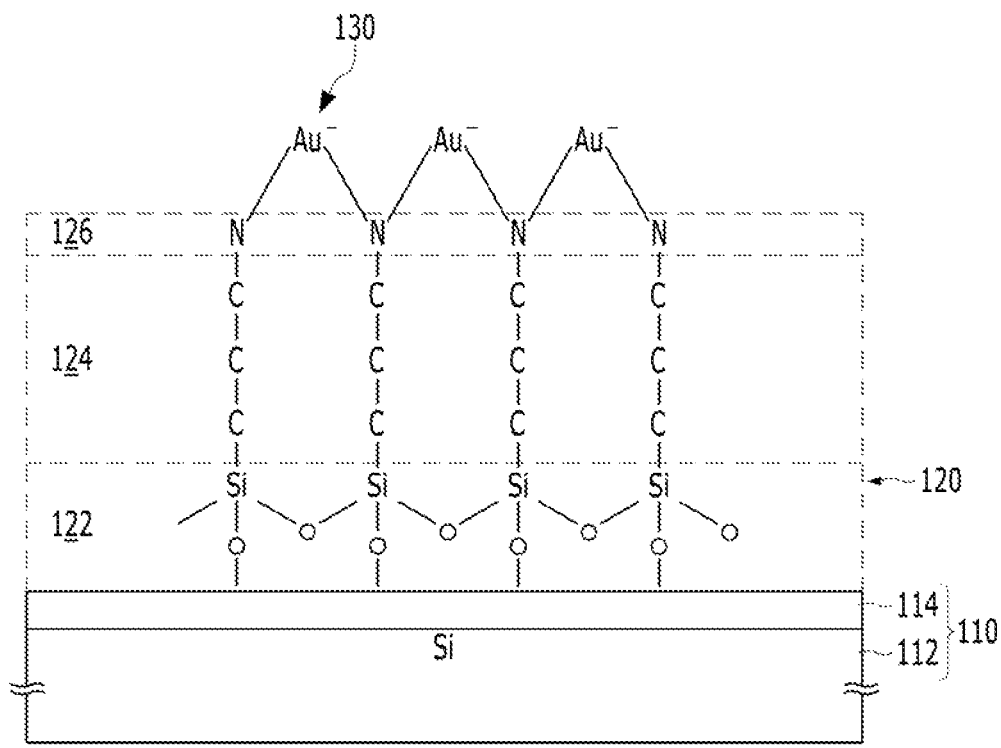
Figure 1D:
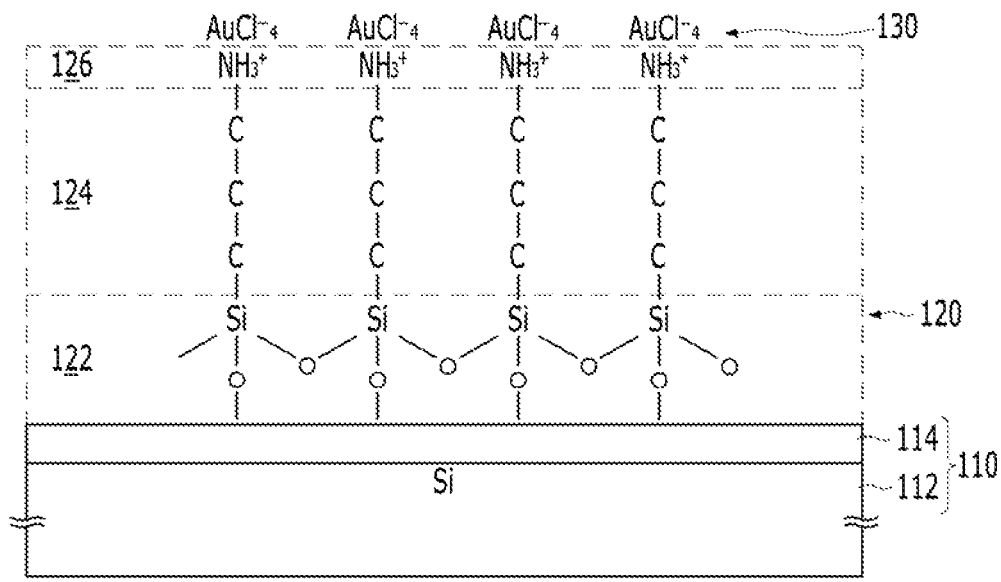
Figure 1E:
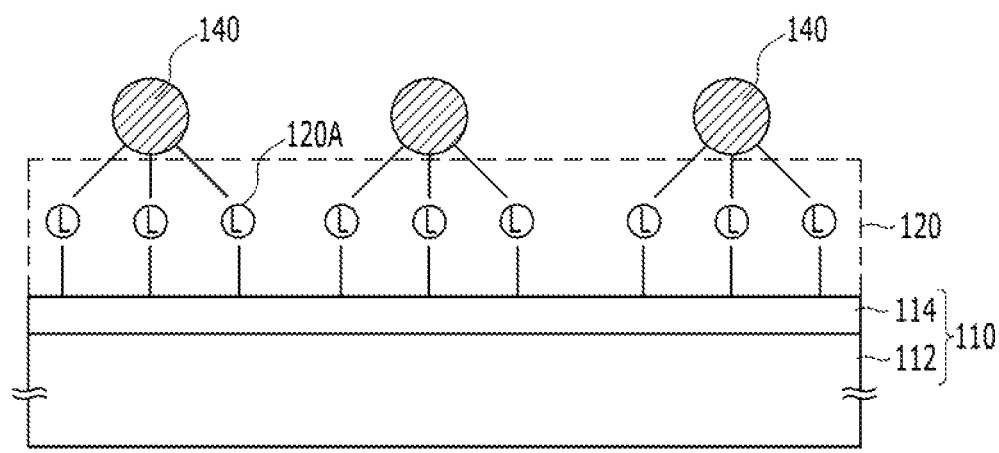

In accordance with the first embodiment of the present disclosure, a method for fabricating a nano structure may include preparing a substrate 110 (see FIG. 1A); bonding linkers 120A to the substrate 110 (see FIG. 1B); bonding metal ions 130 to the linkers 120A (see FIGS. 1C and 1D); and forming (i.e. growing or reducing) the metal ions 130 into metallic nanoparticles 140 by applying energy (see FIG. 1E). The method for fabricating a nano structure may further include supplying a dielectric organic material 150 to the structure including the metallic nanoparticles 140 (see FIG. 1F). Even further, the method for fabricating a nano structure may further include supplying organic surfactants of one or more kinds before the energy is applied, or while applying energy.

FIG. 1A shows the prepared substrate 110. Referring to FIG. 1A, the substrate 110 may have a surface layer 114 having functional groups capable of being bonded to a linkers. For example, the substrate 110 may be a silicon substrate 112 having a silicon oxide ($SiO_2$) layer as the surface layer 114.

The substrate 110 may be a semiconductor substrate, a transparent substrate, or a flexible substrate. The material, structure, and shape of the substrate 110 may differ according to the application device. Also, the substrate 110 may serve as a physical support to the constituent elements of the application device, or the substrate 110 may be a raw material of the constituent elements.

Non-limiting examples of flexible substrates include a flexible polymer substrate formed of polyethylene terephthalate (PET), polyethylene naphthalate (PEN), polyimide (PI), polycarbonate (PC), polypropylene (PP), triacetyl cellulose (TAC), polyethersulfone (PES), polydimethylsiloxane (PDMS), or a mixture thereof. When a flexible substrate is used, the surface layer 114 of the substrate may be made of an organic material having functional groups (e.g., —OH functional group) capable of being bonded to the linkers.

When using a semiconductor substrate, the substrate may be an organic semiconductor, an inorganic semiconductor, or a stacked structure thereof.

Non-limiting examples of inorganic semiconductor substrates include materials selected from the group including group 4 semiconductors, which include silicon (Si), germanium (Ge) and silicon germanium (SiGe); group 3-5 semiconductors, which include gallium arsenide (GaAs), indium phosphide (InP) and gallium phosphide (GaP); group 2-6 semiconductors, which include cadmium sulfide (CdS) and zinc telluride (ZnTe); group 4-6 semiconductors, which include lead sulfide (PbS); and a stack of two or more layers made of different materials selected from these materials. From the perspective of crystallography, the inorganic semiconductor substrate may foe a monocrystalline material, a polycrystalline material, an amorphous material, or a mixture of a crystalline material and an amorphous material. When the inorganic semiconductor substrate is a stacked structure, where two or more layers are stacked, each layer may be a monocrystalline material, a polycrystalline material, an amorphous material, or a mixture of a crystalline material and amorphous material.

To be specific, the inorganic send conductor substrate may be a semiconductor substrate including a wafer, such as a silicon (Si) substrate 112, a silicon substrate with a surface oxide layer, or a Silicon On Insulator (SOI) substrate including a wafer.

When using an organic semiconductor substrate, the organic semiconductor may be an n-type organic semiconductor or a p-type organic semiconductor, which are typically used in the fields of organic transistors, organic solar cells, and organic light emitting diodes (OLED). Non-limiting examples of organic semiconductors include fulleren-derivatives, such as copper-phthalocyanine (CuPc), poly(3-hexylthiophene) (P3HT), pentacene, subphthalocyanines (SubPc), fulleren (C60), [6,6]-phenyl-C61-butyric acid methyl ester (PCBM) and [6,6]-phenyl C70-butyric acid methyl ester (PC70BM), and tetra uorotetracyanoquinodimethane (F4-TCNQ). Again, these are non-limiting examples, and those skilled in the art will appreciate other possibilities that would fall within the spirit and scope of the present invention.

The surface layer 114 of the substrate 110 may be formed of any material that has a functional group capable of being bonded to the linkers. For example, the surface layer 114 may be a single layer or a stacked layer, where two or more layers of different materials are stacked. Where the surface layer 114 is a stacked layer, the dielectric constant of each layer may be different.

To be specific, the surface layer 114 of the substrate 110 may be a single layer of a material selected from the group including an oxide, a nitride, an oxynitride, and a silicate, or a stack of two or more layers, each of which is selected from the group. Non-limiting examples of the surface layer 114 of the substrate 110 include a single layer of at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate, a mixture thereof, and a composite thereof, or a stack of two or more layers, each of which is selected from the group.

The surface layer 114 of the substrate 110 may be a metal thin film. The metal thin film may have a thickness of about 100 nm or less. According to an embodiment of the present disclosure, the metal thin film may have a thickness of about 1 nm to 100 nm. When the metal thin film is extremely thin, about 1 nm or less, the uniformity of the thin film may deteriorate. Non-limiting examples of the material for the metal thin film, which is used as the surface layer 114, may include transition metals including noble metals, metals, and mixtures thereof. Examples of the transition metals include Sc, Y, La, Ac, Ti, Zr, Hf, V, Kb, Ta, Cr, Mo, W, Mn, Te, Re, Fe, Ru, Os, Co, Rh, Ir, Ni, Pd, Pt, Cu, Ag, Au, and mixtures thereof, and examples of the metals include Li, Ha, K, Kb, Cs, Fr, Be, Mg, Ca, Sr, Ba, Ra, Zn, Cd, Al, Ga, In, Tl, Ge, Sn, Pb, Sb, Bi, Po, and mixtures thereof.

The surface layer 114 may be formed through a thermal oxidation process, a physical deposition process, or a chemical deposition process. Non-limiting examples of the physical deposition process and the chemical deposition process include sputtering, magnetron-sputtering, e-beam evaporation, thermal evaporation, Laser Molecular Beam Epitaxy (L-MBE), a Pulsed Laser Deposition (PLD), vacuum deposition, Atomic Layer Deposition (ALD), and Plasma Enhanced Chemical Vapor Deposition (PECVD.

FIG. 1B shows a linker layer 120 formed on the substrate 110. The linker layer 120 may be composed of a plurality of linkers 120A. The linker layer 120 may be a self-assembled monomolecular layer bonded to the surface of the substrate 110.

The linkers 120A may be organic linkers that are chemically bonded to or adsorbed on the surface of the substrate 110 and may chemically bond with metal ions. Specifically, the linkers 120A may be organic linkers having both functional groups 122 that are chemically bonded to or adsorbed on the surface layer 114 of the substrate 110 and functional groups 126 that are chemically bonded to metal ions (to be formed later). The chemical bonds may include a covalent bond, an ionic bond, or a coordination bond. For example, the bond between metal ions and the linkers may be an ionic bond between positively charged (or negatively charged) metal ions and negatively charged (or positively charged) linkers, at least at one end. The bond between the surface layer of the substrate 110 and the linkers may be a bond caused by self-assembly or may be a spontaneous chemical bond between the functional group 122 of the linkers and the surface of the substrate.

The linkers 120A may foe organic monomolecules that form a self-assembled monomolecular layer. In other words, the linkers 120A may be organic monomolecules having both of the functional groups 122 that are bonded to the surface layer 114 and the functional groups 126 capable of being bonded to metal ions. The linkers 120A may include a chain group 124, which connects the functional group 122 with the functional group 126 and enables the formation of a monomolecular layer aligned by Van Der Waals interactions.

Self-assembly may be achieved by suitably designing the material of the substrate surface and the first functional group 122 of the organic monomolecule. A set of end groups of materials that are generally known to be self-assembling may be used.

In a specific non-limiting embodiment, when the surface layer 114 of the substrate 110 is made of oxide, nitride, oxynitride, or silicate, the organic monomolecule that is the linker may be a compound represented by the following Formula 1.

(Formula 1)

R1—C—R2

In Formula 1, R1 represents a functional group that bonds with the substrate, C represents a chain group, and R2 represents a functional group that bonds with metal ions. R1 may be one or more functional groups selected from the group including acetyl, acetic acid, phosphine, phosphonic acid, alcohol, vinyl, amide, phenyl, amine, acryl, silane, cyan and thiol groups. C is a linear or branched carbon chain having 1 to 20 carbon atoms. R2 may be one or more functional groups selected from the group including carboxylic acid, carboxyl, amine, phosphine, phosphonic acid and thiol groups.

In a non-limiting embodiment, the organic monomolecule that is the linker 120A may be one or more selected from a group including octyltrichlorosilane (OTS), hexamethyldisilazane (HMDS), octadecyltrichlorosilane (ODTS), (3-aminopropyl)trimethoxysilane (APS), (3-aminopropyl) triethoxysilane, N-(3-aminopropyl)-dimethyl-ethoxysilane (APDMES), perfluorodecyltrichlorosilane (PFS), mercaptopropyltrimethoxysilane (MPTMS), N-(2-aminoethyl)-3aminopropyltrymethoxysilane, (3-trimethoxysilylpropyl) diethylenetriamine, octadecyltrimethoxysilane (OTMS), (heptadecafluoro-1,1,2,2-tetrahydrodecyl)trichlorosilane (FDTS), dichlorodimethylsilane (DDMS), N-(trimethoxysilylpropyl)ethylenediamine triacetic acid, hexadecanethiol (HDT), and epoxyhexyltriethoxysilane.

In terms of ensuring stable isolation between the nanoparticles and the substrate, the organic monomolecule that is the linker may include an alkane chain group, particularly an alkane chain group having 3 to 20 carbon atoms, and may further include an oxygen-containing moiety. Examples of the oxygen-containing moiety include ethylene glycol (—O—CH$_2$—CH$_2$—), carboxylic acid (—COOH), alcohol (—OH), ether (—O—), ester (—COO—), ketone (—CO—), aldehyde (—COH) and/or amide (—NH—CO—), etc.

Attachment of the linkers 120A may be performed by bringing the substrate 110 into contact with a solution of linkers 120A in a solvent. The solvent that is used to form the linker solution may be any solvent that can dissolve the linkers and be easily removed by volatilization. As is known in the art, when the linker contains a silane group, water for promoting hydrolysis may be added to the linker solution. The contact between the substrate and the linker solution may be performed using any known method to form a self-assembled monomolecular layer on a substrate. In a non-limiting embodiment, the contact between the linker solution and the substrate may be performed using a dipping, micro contact printing, spin-coating, roll coating, screen coating, spray coating, spin casting, flow coating, screen printing, ink jet coating or drop casting method.

When metal ions are fixed to the substrate by the linkers 120A, there are advantages in that damage to the surface layer 114 of the substrate may be prevented, and a uniformly distributed metal ion layer may be formed by self-assembly. Additionally, nanoparticles prepared by application of energy may be stably fixed.

The linkers may include functional groups that chemically bond with metal ions. The surface of the substrate 110 may be modified to form a functional group (linker), and then a metal precursor may be supplied to the surface-modified substrate so that metal ions may bond with the functional group. The functional group may be one or more selected from the group including carboxylic acid, carboxyl, amine, phosphine, phosphonic acid and thiol groups. Formation of the functional group on the substrate surface may be performed using any method. Specific examples of the method for forming the functional group on the substrate surface include plasma modification, chemical modification, and vapor deposition (application) of a compound having a functional group. Modification of the substrate surface may be performed by vapor deposition (application of a compound having a functional group) to prevent surface layer imparity introduction, quality deterioration, and damage.

In a specific non-limiting embodiment, when the surface layer 114 of the substrate 110 is formed of an oxide, a nitride, an oxynitride or a silicate, a functional group (linker) may be formed by a silane compound layer on the substrate 110.

The silane compound layer may be made of an alkoxy silane compound having one or more functional groups selected from a group including carboxylic acid, carboxyl, amine, phosphine, phosphonic acid and thiol groups.

The silane compound may be represented by the following Formula 2:

(Formula 2)

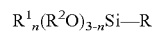

In Formula 2, R$^1$ is hydrogen, a carboxylic acid group, a carboxyl group, an amine group, a phosphine group, a phosphonic acid group, a thiol group, or a linear or branched alkyl group having 1 to 10 carbon atoms; R$^2$ is a linear or branched alkyl group having 1 to 10 carbon atoms; R is a linear or branched alkyl group having 1 to 10 carbon atoms; the alkyl group in R may be substituted with one or more selected from a group including carboxylic acid, carboxyl, amine, phosphine, phosphonic acid and thiol groups; the alkyl group in R$^1$ and the alkyl group in R$^2$ may each be independently substituted with one or more selected from a group including the halogens, carboxylic acid, carboxyl, amine, phosphine, phosphonic acid and thiol groups; and n is 0, 1 or 2.

The silane compound may be represented by one of the following Formulas 3 to 5:

(Formula 3)

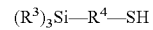

(Formula 4)

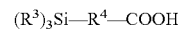

(Formula 5)

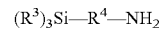

In the Formula 3, 4, and 5, R$^3$ groups are each independently an alkoxy or alkyl group, and one or more R$^3$ groups are an alkoxy group; and R$^4$ is a divalent hydrocarbon group having 1 to 20 carbon atoms. R$^3$ groups in Formulas 3, 4 or 5 may be the same or different and may each be independently an alkoxy group, such as methoxy, ethoxy or propoxy, or an alkyl group; and R$^4$ may be a divalent hydrocarbon group having 1 to 20 carbon atoms, such as —CH$_2$—, —CH$_2$—CH$_2$—, —CH$_2$—CH$_2$—CH$_2$—, —CH$_2$—CH(CH$_3$)—CH$_2$— or —CH$_2$—CH$_2$—CH(CH$_3$)—.

Non-limiting examples of the carboxysilane compound include methyldiacetoxysilane, 1,3-dimethyl-1,3-diacetoxy-disiloxane, 1,2-dimethyl-1,2-diacetoxydisilane, 1,3-dimethyl-1,3-dipropionoxydisilamethane, and 1,3-diethyl-1,3-diacetoxydisilamethane. Non-limiting examples of the aminosilane compound include N-(2-aminoethyl)aminopropyltri(methoxy)silane, N-(2-aminoethyl)aminopropyltri(ethoxy)silane, N-(2-aminoethyl)aminopropylmethyldi(methoxy)silane, N-(2-aminoethyl)aminopropylmethyldi(ethoxy)silane, 3-aminopropyl tri(methoxy)silane, 3-aminopropyltri(ethoxy)silane, 3-aminopropylmethyidi (methoxy) silane, and 3-aminopropylmethyldi (ethoxy) silane. Non-limiting examples of the mercaptosilane compound include mercaptopropyltrimethoxysilane, mercaptopropyltriethoxysilane, mercaptoethyltrimethoxysilane, and mercaptoethyltriethoxysilane.

The above-described silane compound may be applied to or deposited on the surface of the substrate 110 to form a functional group (a functional group resulting from a silane compound layer). The silane compound layer may be formed by applying and drying a silane compound solution. Alternatively, the silane compound may be deposited by supplying a gaseous silane compound to the substrate surface.

As the silane compound functional group will react with a metal precursor (supplied later) to fix metal ions to the substrate, it is preferred to form the silane compound layer where the functional groups are uniformly exposed to the surface. The silane compound layer may be formed by atomic layer deposition (ALD).

The above-described silane compounds having a functional group (particularly the silane compound of Formulas 2, 3, and 4) may belong to the above-described self-assembly molecule group. Specifically, (R$^3$)$_3$Si may correspond to the functional group that is bonded to the substrate surface, $R^4$ may correspond to the chain group, and R (R in formula 2) such as —SH, —COOH or —NH$_2$, may correspond to the functional group that bonds with metal ions. The silane compound layer may be a monomolecular layer formed of the silane compound.

FIG. 1C shows metal ions 130 bonded to the linkers 120A. The metal ions 130 may be bonded to the functional groups 126 of the linkers 120A.

The metal ions 130 may be formed by supplying a metal precursor to the substrate (having the linkers formed thereon). Specifically, the metal ions 130 may be formed by applying (or impregnating) a metal precursor solution to the substrate or applying a gaseous metal precursor to the substrate.

The metal precursor may be designed in view of the material of the desired nanoparticles. For example, the metal precursor may foe precursors of one or more metals selected from a group including transition metals, post-transition metals, and metalloids. In a non-limiting embodiment, the transition metal precursor may be a transition metal salt. Specifically, the transition metal may be one or more selected from a group including Au, Ag, Ru, Pd and Pt, and the transition metal salt may be selected from a group including halides, chalcogenides, hydrochlorides, nitrates, sulfates, acetates or ammonium salts of the transition metal. When the transition metal of the transition metal precursor is Au, examples of the transition metal precursor include, but are not limited to, $HAuCl_4$, $AuCl$, $AuCl_3$, $Au_4Cl_8$, $KAuCl_4$, $NaAuCl_4$, $NaAuBr_4$, $AuBr_3$, $AuBr$, $AuF_3$, $AuF_5$, $AuI$, $AuI_3$, $KAu(CN)_2$, $Au_2O_3$, $Au_2S$, $Au_2S_3$, $AuSe$, $Au_2Se_3$, and the like.

The metal ions 130 that are bonded (attached) to the substrate by the linkers 120A may be ions of one or more metals (elements) selected from a group including transition metals, post-transition metals, and metalloids. Depending on the kind of metal precursor, the metal ions 130 may be the above-described metal ions themselves or monomolecular ions including the above-described metals. Metal ions themselves may be bonded to the functional groups 126 of the organic monomolecules (linkers) (see FIG. 1C), or metal-containing monomolecular ions may be bonded to the second functional groups 126 of organic monomolecules (see FIG. 1D). Metal-containing monomolecular ions may foe ions originating from the metal precursor (ions resulting from the reaction between the organic monomolecules and the functional groups).

FIG. 1E shows metallic nanoparticles 140 formed by the reduction and growth of the metal ions 130 by application of energy. The metallic nanoparticles 140 may foe formed on the substrate 110 by the linkers 120A.

Advanced technology enables the synthesis of very fine nanoparticles from tens to hundreds of atoms, but in view of thermodynamics, synthesized nanoparticles may not have a uniform particle sire distribution and the difference in size between the nanoparticles may increase as the size of the reaction field during synthesis increases. In addition, a method of preparing nanoparticles by etching using a top-down process enables the preparation of particles having a size of about 20 nm or less by advanced lithography, but it is difficult to apply commercially because the process is complicated and requires precise control.

However, in a preparation method according to an embodiment of the present disclosure, nanoparticles are prepared directly in a very small reaction field corresponding to the surface region of the substrate, and thus nanoparticles having a very uniform and finely controlled size may foe prepared at high density. Because nanoparticles are prepared by fixing metal ions to the substrate by the linkers and then applying energy to the metal ions, the nanoparticles may be produced quickly in a simple, easy and cost-effective manner. Further, because nucleation and growth (formation of nanoparticles) are induced by application of energy in a state where metal atoms (ions) are fixed to the substrate by the linkers, migration of the metal atoms (ions) may be uniformly controlled resulting in the formation of more uniform and fine nanoparticles. The metal material to be used for nucleation and growth to form nanoparticles may be supplied only by the metal atoms (ions) bonded to the linkers. In other words, the supply of material used to form nanoparticles comes from the diffusion of the metal atoms (ions) bonded to the linkers. Due to bonding of the metal atoms (ions) to the linkers, the metal atoms (ions) have difficulty migrating beyond a predetermined distance to participate in nucleation and growth, and thus the reaction field of each nanoparticle may be limited to around the nucleus. Thus, nanoparticles having a more uniform and finer size may be formed on the substrate at high density and the separation distance between the formed nanoparticles may also be uniform. In addition, bonding of the metallic nanoparticles to the linkers is maintained, and thus the nanoparticles may be stably fixed to the substrate by the linkers. Also, the separation distance between the nanoparticles may correspond to the diffusion distance of the metal atoms that participate in the nucleation and growth of the nanoparticles.

Energy that is applied to form the nanoparticles may be one or more selected from among heat energy, chemical energy, light energy, vibration energy, ion beam energy, electron beam energy, and radiation energy.

Thermal energy may include Joule heat and may be applied directly or indirectly. Direct application of thermal energy may be performed in a state in which a heat source and the substrate having metal ions fixed thereto come into physical contact with each other. Indirect application of thermal energy may be performed in a state in which a heat source and the substrate having metal ions fixed thereto do not come into physical contact with each other. Non-limiting examples of direct application include a method of placing a heating element, which generates Joule heat by the flow of electric current, beneath the substrate and transferring thermal energy to the metal ions through the substrate. Non-limiting examples of indirect application include using a conventional heat-treatment furnace including a space in which an object (such as a tube) to be heat-treated is placed, a heat insulation material that surrounds the space to prevent heat loss, and a heating element placed inside the heat insulation material. A non-limiting example of indirect heat application is seen in the method of placing a heating element at a predetermined distance above the substrate, where the metal ions are fixed, and transferring thermal energy to the metal ions through a fluid (including air) present between the substrate and the heating element.

Light energy may include light having a wavelength ranging from extreme ultraviolet to near-infrared, and application of light energy may include irradiation with light. In a non-limiting embodiment, a light source may be placed above the substrate, having the metal ions fixed thereto, at a predetermined distance from the metal ions, and light from the light source may be irradiated onto the metal ions.

Vibration energy may include microwaves and/or ultrasonic waves. Application of vibration energy may include irradiation with microwaves and/or ultrasonic waves. In a non-limiting embodiment, a microwave and/or ultrasonic wave source may be placed above the substrate, having the metal ions fixed thereto, at a predetermined distance from the metal ions, and microwaves and/or ultrasonic waves from the source may be irradiated onto the metal ions.

Radiation energy may include one or more selected from a group including α rays, β rays and γ rays and may be β rays and/or γ rays in terms of reduction of the metal ions. In a non-limiting embodiment, a radiation source may be placed above the substrate, having the metal ions fixed thereto, at a predetermined distance from the metal ions, and radiation from the source may be irradiated onto the metal ions.

Energy may be kinetic energy of a particle beam, and the particle beam may include an ion beam and/or an electron beam. The ions of the beam may be negatively charged. In a non-limiting embodiment, an ion or electron source may be placed above the substrate, having the metal ions fixed thereto, at a predetermined distance from the metal ions, and an ion beam and/or electron beam may be applied to the metal ions using an accelerating element that provides an electric field (magnetic field) that accelerates ions or electrons in the direction of the metal ions.

Chemical energy is the Gibbs free energy difference between before and after a chemical reaction, and the chemical energy may include reduction energy. Chemical energy may include the energy of a reduction reaction with a reducing agent arid may mean the energy of a reduction reaction in which the metal ions are reduced by the reducing agent. In a non-limiting embodiment, application of chemical energy may be a reduction reaction in which the reducing agent is brought into contact with the substrate having the metal ions fixed thereto. The reducing agent may be supplied in the liquid or gaseous state.

In a fabrication method according to an embodiment of present disclosure, application of energy may include simultaneously or sequentially applying two or more selected from among heat energy, chemical energy, light energy, vibration energy, ion beam energy, electron beam energy, and radiation energy.

In a specific embodiment of simultaneous application, application of heat may be performed simultaneously with, application of a particle beam. The particles of the particle beam may be heated by heat energy. In another specific embodiment of simultaneous application, application of heat may be performed simultaneously with application of a reducing agent. In still another embodiment of simultaneous application, application of a particle beam may be performed simultaneously with application of infrared rays or with application, of microwaves.

Sequential application may mean that one kind of energy is applied followed by application of another kind of energy. It may also mean that different kinds of energy are continuously or discontinuously applied to the metal ions. It is preferable that reduction of the metal ions fixed to the substrate by the linkers be performed before formation of nanoparticles, and thus in a specific embodiment of sequential application, heat may be applied after addition of a reducing agent or after application of a positively charged particle beam.

In a non-limiting practical embodiment, application of energy may be performed using a rapid thermal processing (RTP) system including a tungsten-halogen lamp, and the rapid thermal processing may be performed at a heating rate of 50 to 150° C./sec. Also, rapid thermal processing may be performed in a reducing atmosphere or an inert gas atmosphere.

In a non-limiting practical embodiment, application of energy may be performed by bringing a solution of a reducing agent into contact with the metal ions followed by thermal processing using the rapid thermal processing system in a reducing atmosphere or an inert gas atmosphere.

In a non-limiting practical embodiment, application of energy may be performed by generating an electron beam from an electron beam generator in a vacuum chamber and accelerating the generated electron beam to the metal ions. The electron beam generator may be a square type or a linear gun type. The electron beam may be produced by generating plasma from the electron beam generator and extracting electrons from the plasma using a shielding membrane. In addition, a heating element may be provided on a holder for supporting the substrate in the vacuum chamber, and heat energy may be applied to the substrate by this heating element before, during and/or after application of the electron beam.

When the desired nanoparticles are metal nanoparticles, the metal nanoparticles may be prepared in situ by application of energy as described above. When the nanoparticles to be prepared are not metal nanoparticles, but are metal compound nanoparticles, the metal compound nanoparticles may be prepared by supplying an element different from the metal ions during or after application of the above-described energy. Specifically, the metal compound nanoparticles may include metal oxide nanoparticles, metal nitride nanoparticles, metal carbide nanoparticles or intermetallic compound nanoparticles. More specifically, the metal compound nanoparticles may be prepared by supplying a different element in the gaseous or liquid state during or after application of the above-described energy. In a specific embodiment, metal oxide nanoparticles in place of metal nanoparticles may be prepared by supplying an oxygen source including oxygen gas during application of energy. In addition, metal nitride nanoparticles in place of metal nanoparticles may be prepared by supplying a nitrogen source including nitrogen gas during application of energy. Metal carbide nanoparticles may be prepared by supplying a carbon source, including $C_1$-$C_{10}$ hydrocarbon gas during application of energy, and intermetallic compound nanoparticles may be prepared by supplying a precursor gas containing a different element, which provides an intermetallic compound, during application of energy. Specifically, the intermetallic compound nanoparticles may be prepared by carbonizing, oxidizing, nitrifying or alloying the metal nanoparticles prepared by application of the above-described energy.

The density of nanoparticles (the number of nanoparticles per unit surface area of the channel region) and the particle sire and particle size distribution may be controlled by the energy application conditions, including the kind, magnitude, temperature, and duration of energy application.

To be specific, nanoparticles having an average particle diameter of about 0.5 nm to 3 nm may foe fabricated by applying energy. In this case, uniform nanoparticles may be prepared with a particle radius standard deviation of about ±20% or less, and highly dense nanoparticles having a nanoparticle density (which is the number of the nanoparticles per unit area) of about $10^{13}$ to $10^{15}/cm^2$ may be prepared.

According to an embodiment, when the applied energy is electron beam, the electron beam may be irradiated at a dose of about 0.1 KGy to 100 KGy. With the irradiation dose of the electron beam, nanoparticles having an average particle diameter of about 2 to 3 nm may be prepared, and the nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.1 \times 10^{14}$ to $10 \times 10^{14}$/cm$^2$.

According to another embodiment, when the applied energy is an electron beam, the electron beam may be irradiated at a dose of about 100 µGy to 50 KGy. With the irradiation dose of the electron beam, nanoparticles having an average particle diameter of about 1.3 to 1.9 nm may be prepared, and the nanoparticles may have a particle radius standard deviation of about ±20% or less. The prepared nanoparticle density (which is the number of the nanoparticles per unit area) may range from about $10^{13}$ to $10^{15}$/cm$^2$, and, specifically, the nanoparticle density may range from about $0.2 \times 10^{14}$ to $20 \times 10^{14}$/cm$^2$.

According to another embodiment, when the applied energy is electron beam, the electron beam may be irradiated at a dose of about 1 µGy to 10 KGy. With the irradiation dose of electron beam, nanoparticles having an average particle diameter of about 0.5 to 1.2 nm may be prepared, and nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.2 \times 10^{14}$ to $30 \times 10^{14}$/cm$^2$.

According to another embodiment, when the applied energy is heat energy, nanoparticles having an average particle diameter of about 2 to 3 nm may be prepared by performing a heat treatment in a reducing atmosphere at a temperature of about 100 to 500° C. for about 0.5 to 2 hours or by supplying a reducing agent to the metal ions bonded to the linkers and performing a heat treatment in an inert gas atmosphere at a temperature of about 200 to 400° C. for about 0.5 to 2 hours. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.1 \times 10^{14}$ to $10 \times 10^{14}$/cm$^2$.

According to another embodiment, when the applied energy is heat energy, nanoparticles having an average particle diameter of about 1.3 to 1.9 nm may be prepared by performing a heat treatment in a reducing atmosphere at a temperature of about 200 to 400° C. for about 0.5 to 2 hours or by supplying a reducing agent to the metal ions bonded to the linkers and performing a heat treatment in an inert gas atmosphere at a temperature of about 100 to 300° C. for about 0.5 to 2 hours. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.2 \times 10^{14}$ to $20 \times 10^{14}$/cm$^2$.

According to another embodiment, when the applied energy is heat energy, nanoparticles having an average particle diameter of about 0.5 to 1.2 nm may be prepared by performing a heat treatment in a reducing atmosphere at a temperature of about 200 to 400° C. for about 0.2 to 1 hour or by supplying a reducing agent to the metal ions bonded to the linkers and performing a heat treatment in an inert gas atmosphere at a temperature of about 100 to 300° C. for about 0.2 to 1 hour. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.2 \times 10^{14}$ to $30 \times 10^{14}$/cm$^2$.

According to another embodiment, when the applied energy is chemical energy, nanoparticles having an average particle diameter of about 2 to 3 nm may be prepared by performing a chemical reaction with a reducing agent at a reaction temperature of about 20 to 40° C. for about 0.5 to 2 hours. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.1 \times 10^{14}$ to $10 \times 10^{14}$/cm$^2$.

According to another embodiment, when the applied energy is chemical energy, nanoparticles having an average particle diameter of about 1.3 to 1.9 nm may be prepared by performing a chemical reaction induced by a reducing agent at a reaction temperature of about −25 to 5° C. for about 0.5 to 2 hours. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.2 \times 10^{14}$ to $20 \times 10^{14}$/cm$^2$.

According to another embodiment, when the applied energy is chemical energy, nanoparticles having an average particle diameter of about 0.5 to 1.2 nm may be prepared by performing a chemical reaction induced by a reducing agent at a reaction temperature of about −25 to 5° C. for about 0.2 to 1 hour. The prepared nanoparticles may have a particle radius standard deviation of about ±20% or less. The prepared nanoparticle density (which is the number of the nanoparticles per unit area) may range from about $10^{13}$ to $10^{15}$/cm$^2$, and specifically, the nanoparticle density may range from about $0.2 \times 10^{14}$ to $30 \times 10^{14}$/cm$^2$.

As described above, nanoparticles may be grown by applying heat energy and/or chemical energy in a reducing atmosphere. When heat energy is applied in a reducing atmosphere, the reducing atmosphere may contain hydrogen. In a specific embodiment, the reducing atmosphere may be an inert gas containing about 1 to 5% hydrogen. In terms of providing uniform reduction, heat energy may foe applied in an atmosphere in which a reducing gas flows. In a specific embodiment, the atmosphere may have reducing gas flowing at a rate of about 10 to 100 cc/min. When chemical energy and heat energy are to be sequentially applied, a reducing agent may be brought into contact with the metal ions, followed by application of heat energy in an inert atmosphere. The reducing agent may be any compound that reduces the metal ions into a metal. When chemical energy is applied by addition of the reducing agent, transition metal nanoparticles may also be formed by a reduction reaction. When nanoparticles are to be formed from the metal ions by a reduction reaction, the reduction reaction should occur very rapidly and uniformly throughout the channel region so that transition metal particles having a more uniform size may be formed. A strong reducing agent may be used, and in a preferred embodiment, the reducing agent may be $NaBH_4$, $KBH_4$, $N_2H_4H_2O$, $N_2H_4$, $LiAlH_4$, $HCHO$, $CH_3CHO$, or a mixture of two or more thereof. Also, when chemical energy is applied, the size of the nanoparticles may be controlled by adjusting the chemical reaction temperature and controlling the nucleation rate and the growth of the nanoparticles when a strong reducing agent as described above, is used. The contact between the metal ions bonded to the junkers and the reducing agent may be achieved either by applying a solution of the reducing agent to the metal ion bonded region, or by impregnating the substrate with a solution of the reducing agent, or by supplying the reducing agent in the gaseous phase to the substrate. In a specific non-limiting embodiment, the contact between the reducing agent and the metal ions may be performed at room temperature for about 1 to 12 hours.

As described above, the nucleation and growth of transition metal nanoparticles may be controlled by one or more factors selected from among the kind, magnitude, and duration of the applied energy.

Meanwhile, it is possible to prepare not only metallic nanoparticles but also metal oxide nanoparticles, metal nitride nanoparticles, metal carbide nanoparticles, or intermetallic compound nanoparticles by supplying a heterogeneous atom source while energy is applied or after energy is applied to change metallic nanoparticles into metallic compound nanoparticles.

In a fabrication method according to an embodiment of the present disclosure, i) the sire of nanoparticles may be controlled by supplying an organic surfactant that is bonded to or adsorbed on the metal ions, followed by application of energy. Otherwise, ii) the size of nanoparticles may be controlled during the growth thereof by supplying an organic surfactant that is to be bonded to or adsorbed on the metal ions during application of energy. This supply of the organic surfactant may be optionally performed during the fabrication process. Instead of a single organic surfactant that is applied before or during application of energy, a plurality of organic surfactants may be used.

To more effectively inhibit the mass transfer of the metal ions, a first organic material and a second organic material that are different from each other may be used as the surfactant.

The first organic material may be a nitrogen- or sulfur-containing organic compound. For example, the sulfur-containing organic material may include a linear or branched hydrocarbon compound having a thiol group at one end. In a specific example, the sulfur-containing organic compound may be one or more selected from a group including HS—$C_n$—$CH_3$ (n: an integer ranging from 2 to 20), n-dodecyl mercaptan, methyl mercaptan, ethyl mercaptan, butyl mercaptan, ethylhexyl mercaptan, isooctyl mercaptan, tert-dodecyl mercaptan, thioglycolacetic acid, mercaptopropionic acid, mercaptoethanol, mercaptopropanol, mercaptobutanol, mercaptohexanol and octyl thioglycolate.

The second organic material may be a phase-transfer catalyst-based organic compound, for example, quaternary ammonium or a phosphonium salt. More specifically, the second organic surfactant may be one or more selected from a group including tetraocylyammonium bromide, tetraethylammonium, tetra-n-butylammonium bromide, tetramethylammonium chloride, and tetrabutylammonium fluoride.

The organic surfactant that is applied before or during application of energy may be bonded to or adsorbed on the nuclei of metal ions or the metal ions bonded to the linkers, and the nucleation and growth of nanoparticles by energy applied may be controlled by the organic surfactant that is bonded to or adsorbed on the metal ions. This organic surfactant makes it possible to inhibit the mass transfer of the metal ions during application of energy to thereby form more uniform and finer nanoparticles. Because the metal ions bond with the organic surfactant, these metal ions require higher activation energy compared to when they diffuse in order to participate in nucleation or growth, or the diffusion thereof is physically inhibited by the organic surfactant. Thus, the diffusion of the metal atoms (ions) may be slower and the number of metal atoms (ions) that participate in the growth of nuclei may be decreased.

The process of applying energy in the presence of the organic surfactant may include, before application of energy, applying a solution of the organic surfactant to the channel region (i.e., the substrate surface having the metal ions bonded thereto by the linkers) or supplying the organic surfactant in the gaseous state to the channel region. Alternatively, it may include, together with application of energy, applying a solution of the organic surfactant to the channel region having the metal ions formed therein or supplying the organic material in the gaseous state to the channel region to bond or adsorb the organic surfactant to the metal nuclei. Alternatively, it may include, during application of energy, applying a solution of the organic surfactant to the channel region having the metal ions formed therein or supplying the organic material in the gaseous state to the channel region to bond or adsorb the organic surfactant to the metal nuclei. Alternatively, it may include, after application of energy for a predetermined period of time and then pausing application of energy, applying a solution of the organic surfactant to the channel region having the metal ions formed therein or supplying the organic material in the gaseous state to the channel region to bond or adsorb the organic surfactant to the metal nuclei, followed by re-application of energy.

In a fabrication method according to a first embodiment of the present disclosure, energy may be applied to the entire area or a portion of the region having the metal ions bonded thereto. When energy is applied to a portion of the region, energy may be irradiated in a spot, line or predetermined plane shape. In a non-limiting embodiment, energy may be applied (irradiated) in spots while the entire metal ion-bonded region may be scanned. Application of energy to a portion of the metal ion-bonded region may include not only irradiating energy in a spot, line or plane shape while the metal ion-bonded region is entirely scanned, but also includes where energy is applied (irradiated) only to a portion of the metal ion-bonded region. As described above, a pattern of nanoparticles may be formed by applying energy to a portion of the channel region. In other words, application (irradiation) of energy to a portion of the channel region makes it possible to form a pattern of nanoparticles.

Figure 1F:
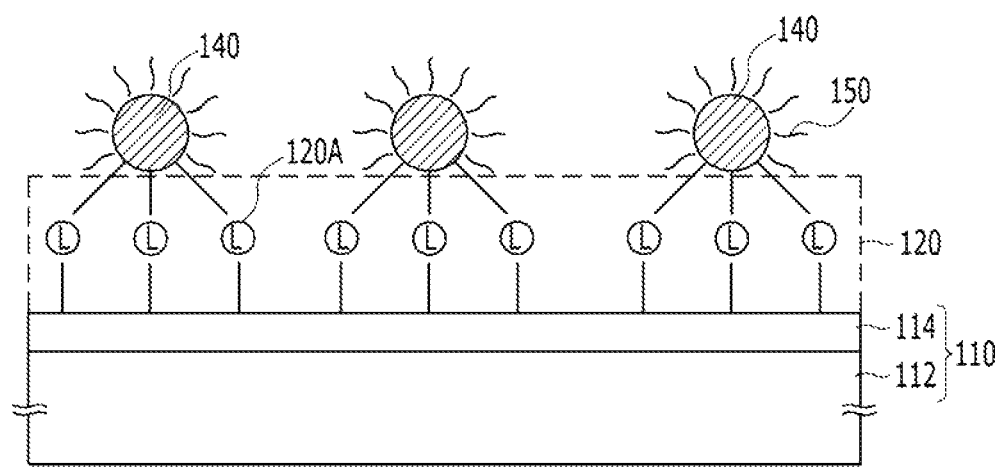

FIG. 1F shows a dielectric organic material 150 bonded to the metallic nanoparticles 140 grown by application of energy. The dielectric organic material 150 may be in a state in which it coats the surface of the metallic nanoparticles 140 or fills the gaps between the metallic nanoparticles 140. The dielectric: organic material 150 may provide isolation between the nanoparticles to more reliably prevent the flow of current between nanoparticles.

If a sufficient amount of the organic surfactant was supplied in the preceding action, that is, if the organic surfactant that is applied before or during application of energy remains on the surface of the grown nanoparticles to provide sufficient isolation between the grown nanoparticles, the dielectric organic material 150 does not need to be added to the surface of the grown nanoparticles 140. In other words, because whether the organic material is to be used before or during application of energy (or the supply or kind of organic material, etc.) is determined according to the size of nanoparticles to be formed, the formation of the dielectric organic material 150 after the nanoparticles 140 have been grown is optional.

Supply of the dielectric organic material 150 may be performed by applying a solution of the dielectric organic material to the nanoparticle layer formed by application of energy, and then drying the applied solution, thereby filling the dielectric organic material into the gaps between the nanoparticles. This may provide a structure in which the nanoparticles are embedded in a dielectric matrix made of the dielectric organic material. The dielectric organic material that Is used in the present disclosure may be any conventional dielectric material that is used, to form dielectric layers in conventional organic-based electronic devices. Specific examples of the dielectric organic material include, but are not limited to, benzocyclobutene (BCB), acrylic compounds, polyimide, polymethylmethacrylate (PIMA), polypropylene, fluorinated compounds (e.g., CYTOPTM), polyvinyl alcohol, polyvinyl phenol, polyethylene terephthalate, poly-p-xylylene, cyanopulluane (CYMM) and polymethylstyrene.

The dielectric organic material 150 may be a substance that spontaneously bonds with a metal. In other words, after the formation of nanoparticles by application of energy, the dielectric organic material may be bonded to the metal of the nanoparticles (i.e., the metal of the metal ions attached to the substrate by the linkers) either by applying to the channel region a solution of the dielectric organic material that spontaneously bonds with the metal of the metal ions attached to the substrate by linkers, or by supplying the dielectric organic material in the gaseous state to the channel region, thereby forming composite nanoparticles having a core-shell structure including nanoparticle cores and dielectric shells. According to this method, a very uniform dielectric layer may be formed on fine nanoparticles, and more reliable isolation between the nanoparticles may be ensured.

The dielectric organic material 150 that is used in the present disclosure may be any dielectric material having a functional group that bonds with the metal contained in the nanoparticles. In a specific embodiment, the dielectric organic material that spontaneously bonds with the metal contained in the nanoparticles may include, at one end, a functional group such as a thiol group (—SH), a carboxyl group (—COOH) and/or an amine group (—NH$_2$) that may spontaneously form a chemical bond with the metal contained in the nanoparticles, and at the other end, a functional group such as a methyl group that does not react with the metal contained in the nanoparticles, and as the backbone, an alkane chain that enables the formation of a uniform dielectric layer. The thickness of the dielectric layer (shell) may be controlled by the carbon number of the alkane chain, and the dielectric organic material may have a $C_3$-$C_{20}$ alkane chain.

As an example, when the layer formed of the metallic nanoparticles 140 and the dielectric organic material 150 is applied to a floating gate of a flash memory cell, the weight ratio between the metallic nanoparticles and the dielectric organic material in the floating gate may be about 1:0.5 to 10. This weight ratio between the metallic nanoparticles and the dielectric organic material may stably prevent current from flowing through the nanoparticles and provide the floating gate with physical stability. This weight ratio between the nanoparticles and the dielectric organic material may be controlled by the amount of dielectric organic material that is supplied to the substrate having the nanoparticles formed therein. In addition, when a dielectric organic material spontaneously bonds with the surface of the nanoparticles, the weight ratio between the nanoparticles and the dielectric material may also be controlled by the carbon number of the alkane chain of the dielectric organic material, as described above.

In order to more securely fix the nanoparticles 140 having the dielectric organic material 150 formed thereon, a layer of an inorganic oxide may additionally be formed. The inorganic oxide layer may be formed directly on the nanoparticles without the dielectric organic material. The organic oxide layer may be formed by a conventional vapor deposition or a liquid dipping method.

Referring to FIG. 1F, the nano structure formed through the fabrication method in accordance with the first embodiment of the present invention is described in detail.

Referring to FIG. 1F, the nano structure in accordance with the first embodiment of the present invention may include a substrate 110, linkers 120A formed over the substrate 110, and metallic nanoparticles 140 that are grown from metal ions bonded to the linkers 120A. The nano structure may further include a dielectric organic material 150 bonded to the surface of the metallic nanoparticles 140.

The substrate 110 may include a surface layer 114 having functional groups capable of being bonded to the linkers 120A. The surface layer 114 may include an oxide layer. To be specific, non-limiting examples of the surface layer 114 of the substrate 110 may be a layer of at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, and a hafnium silicate.

The substrate 110 may be a flexible substrate, which may include a surface layer having a hydroxyl (—OH) functional group, The flexible substrate may include one or a mixture of two or more selected from the group including polyethylene terephthalate (PET), polyethylene naphthalate (PEN), polyimide (PI), polycarbonate (PC), polypropylene (PP), triacetyl cellulose (TAG), polyethersulfone (PES), and polydimethylsiloxane (PDMS).

The linkers 120A may be organic monomolecules bonded to the surface of the substrate 110 through self-assembly. The nano structure may include a linker layer 120 formed of the plurality of the linkers 120A bonded to the surface of the substrate 110. The linker layer 120 may be a self-assembled monomolecular layer formed to be self-combined with the surface of the substrate 110. Also, the linker layer 120 may be a silane compound layer having one functional group selected, from the group including an amine group, a carboxylic acid group, and a thiol group. The linkers 120A may include one functional group selected from the group including an amine group, a carboxylic acid group, and a thiol group. Each of the linkers 120A may include first functional groups (which are denoted by 122 in FIG. 1B) bonded to the surface of the substrate 110, second functional groups (which are denoted by 126 in FIG. 1B) bonded to metal ions, and chain groups (which are denoted by 124 in FIG. 1B) for connecting the first functional groups and the second functional groups to each other.

The metallic nanoparticles 140 may be selected from the group including metal nanoparticles, metal oxide nanoparticles, metal nitride nanoparticles, metal carbide nanoparticles, and intermetallic compound nanoparticles. The metallic nanoparticles 140 may be grown by bonding metal ions to the linkers 120A and then growing the metallic nanoparticles 140.

The size of the metallic nanoparticles 140 may be controlled according to the energy application conditions while the metallic nanoparticles 140 are grown. Also, the size of nanoparticles may be controlled before the energy for growing the metallic nanoparticles 140 is applied, or during energy application, by whether a surfactant is supplied or not. The surfactant may be an organic surfactant, and the surfactant may remain on the surface of the metallic nanoparticles 140 after the growing of the metallic nanoparticles 140 is finished, According to an embodiment of the present disclosure, when no surfactant is used, the metallic nanoparticles 140 may have a particle diameter of about 2.0 to 3.0 nm. According to another embodiment of the present disclosure, when a single kind of surfactant is used, the metallic nanoparticles 140 may have a particle diameter of about 1.3 to 1.6 nm. According to another embodiment of the present disclosure, when a plurality of different kinds of surfactants is used, the metallic nanoparticles 140 may have a particle diameter of about 0.5 to 1.2 nm.

The dielectric organic material 150 may be bonded to the surface of the grown metallic nanoparticles 140. The dielectric organic material 150 may prevent current from flowing through the metallic nanoparticles 140. The surface of the metallic nanoparticles 140 may be coated with the dielectric organic material 150, and the dielectric organic material 150 may fill the space between the metallic nanoparticles 140 that are spaced apart from each other. When a surfactant is supplied to the metal ions, which are the state of the metallic nanoparticles 140 before the metallic nanoparticles 140 are grown, or while nanoparticles are growing, the surfactant may remain on the surface of the metallic nanoparticles 140. Since the surfactant may be a dielectric organic material, if the arranged nanoparticles are insulative to each other by the surfactant remaining after the nanoparticles are grown, a further application of dielectric organic material 150 may not be necessary after the nanoparticles 140 are grown.

Although not illustrated in the drawing, an additional dielectric material may be formed between the metallic nanoparticles 140 that are coated with the dielectric organic material 150. In other words, while the dielectric organic material 150 is formed, an inorganic oxide material may be additionally formed in order to fix the metallic nanoparticles 140 more stably. Also, an inorganic oxide material may be formed directly without the dielectric organic material 150.

The metallic nanoparticles 140 may be arranged spaced apart from each other over the linker layer 120 to form a monomolecular nanoparticle layer. The nanoparticle layer may include a dielectric material bonded to the surface of the metallic nanoparticles 140. The dielectric material may include at least one from a group including an organic surfactant, a dielectric organic material, and an inorganic oxide.

The nano structure in accordance with the first embodiment of the present disclosure may have a vertical multi-stack structure. In other words, the nano structure may have a stacked structure where the linker layer 120 and the nanoparticle layer are stacked alternately and repeatedly. A dielectric layer capable of being bonded to the linkers of the upper linker layer may be further included. If a dielectric material forming the lower nanoparticle layer has a functional group capable of being bonded to the linkers of the upper linker layer, an additional dielectric layer may not have to be formed between the lower nanoparticle layer and the upper linker layer. In short, whether to form the dielectric layer between the lower nanoparticle layer and the upper linker layer may be decided based on the kind of the dielectric material that forms the nanoparticle layer.

[Nano Structure and Fabrication Method Thereof in Accordance with a Second Embodiment of the Present Invention]

FIGS. 2A to 2E are cross-sectional views describing a nano structure and a method for fabricating the nano structure in accordance with a second embodiment of the present disclosure.

Figure 2A:
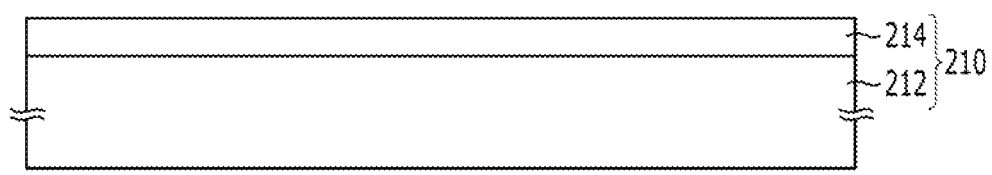
FIGS. 2A to 2E are cross-sectional views describing a nano structure and a method for fabricating the nano structure in accordance with a second embodiment of the present disclosure.
Figure 2B:
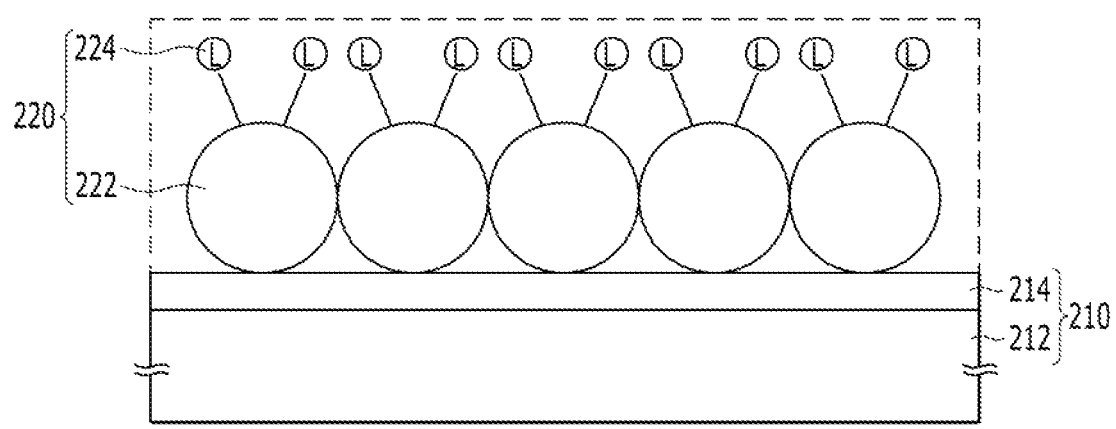
Figure 2C:
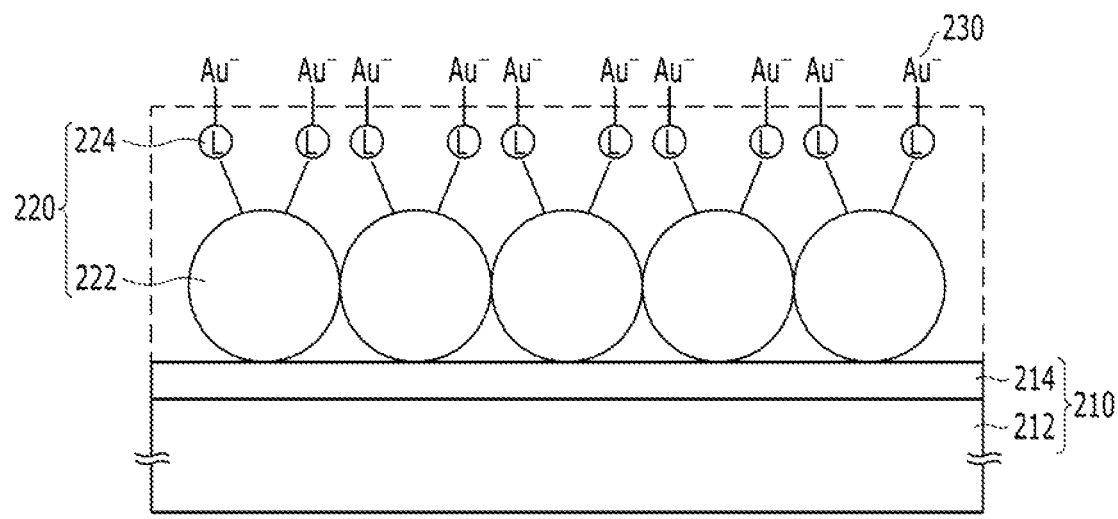
Figure 2D:
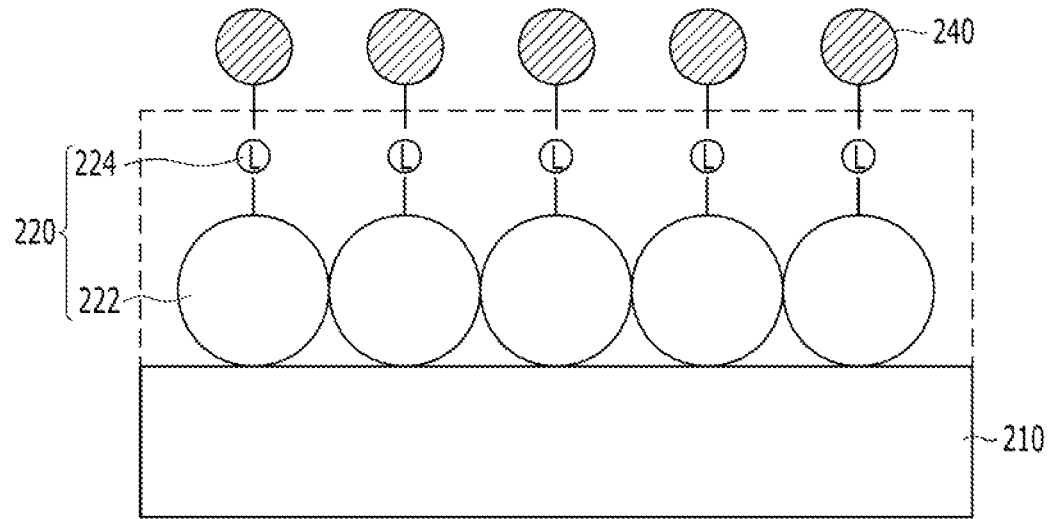

The method for fabricating the nano structure in accordance with the second embodiment of the present disclosure may include preparing a substrate 210 (refer to FIG. 2A), forming dielectric particle supporters 222 where linkers 224 are bonded on the substrate 210 (refer to FIG. 2B), bonding metal ions 230 to the linkers 224 (refer to FIG. 2C), and changing (i.e. forming, reducing, or growing) the metal ions 230 into metallic nanoparticles 240 by applying energy to the metallic nanoparticles 240 (refer to FIG. 2D). The method may further include supplying a dielectric organic material to the structure where the metallic nanoparticles 240 are formed (refer to FIG. 2E). Also, the method may further include supplying one or a plurality of organic surfactants before the energy is applied or during the application of energy.

FIG. 2A shows the substrate 210 prepared. The substrate 210 may have a surface layer 214. For example, the substrate 210 may be a silicon substrate 212 having an oxide layer as the surface layer 214.

The substrate 210 may be a flexible substrate or a transparent substrate. When a flexible substrate 210 is used, the surface layer 214 may be an organic material having a hydroxyl (—OH) functional group.

Non-limiting examples of the flexible substrate include one or a mixture of two or more selected from the group including polyethylene terephthalate (PET), polyethylene naphthalate (PEN), polyimide (PI), polycarbonate (PC), polypropylene (PP), triacetyl cellulose (TAC), polyethersulfone (PES), and polydimethylsiloxane (PDMS). Non-limiting examples of the transparent substrate include a glass substrate and a transparent plastic substrate.

The substrate 210 may be a structure where all or part the constituent elements of an application device are already formed. The substrate 210 may be a wafer, a film, or a thin film, and the surface of the substrate 210 may be nano-patterned (structuralized) in consideration of the physical shape of the application device that is designed along with a transistor having a recess structure or a three-dimensional structure.

In the second embodiment of the present disclosure, the substrate 210 may have the materials and structures described in reference to the first embodiment of the present disclosure, and for the sake of brevity they will not be described again.

FIG. 2B shows the dielectric particle supporters 222 where the linkers 224 are bonded. The dielectric particle supporters 222 where the linkers 224 are bonded may form a supporter layer 220.

A method for forming the supporter layer 220 where the linkers 224 are bonded over the substrate 210 may include preparing a supporter layer material by mixing a dielectric material in a linker solution obtained by dissolving the linkers 224 in a solvent, and depositing the supporter layer material on the substrate 210. The supporter layer material may be applied on the substrate 210 using a spin-coating method, or a liquid deposition method of immersing the substrate 210 in a solution where the supporter layer material is dissolved may be used.

The dielectric particle supporters 222 may include an oxide having at least one element selected from the group including metals, transition metals, post-transition metals, and metalloids. Also, the dielectric particle supporters 222 may include at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate and polymers.

The linkers 224 may be organic monomolecules that are capable of being chemically bonded to or adsorbed on the surface of the dielectric particle supporters 222 and of being chemically bonded to the metal ions 230. To be specific, the linkers 224 may be organic monomolecules that include a first functional group capable of being chemically bonded to or adsorbed on the surface of the dielectric particle supporters 222 and a second functional group capable of being chemically bonded to metal ions, which are to foe formed subsequently. The linkers 224 may also include a chain functional group 124 for connecting the first functional group and the second functional group to each other. The linkers 224 may include one functional group capable of being bonded to metal ions which is selected from the group including an amine group, a carboxylic acid group, and a thiol group. The linkers 224 may be formed of the same or similar materials through diverse methods as described in reference to the first embodiment of the present disclosure.

FIG. 2C shows metal ions 230 bonded to the linkers 224. The metal ions 230 may foe bonded to the functional groups of the linkers 224. The metal ions 230 may be formed by supplying a metal precursor to the substrate (having the linkers formed thereon). Specifically, the metal ions 230 may be formed by applying a metal precursor solution to the substrate 210 or by applying a gaseous metal precursor to the substrate 210. In the second embodiment of the present disclosure, the method for bonding the metal ions 230 to the linkers 224 and the materials used for the method may be as diverse as in the description of the first embodiment of the present disclosure.

FIG. 2D shows metallic nanoparticles 240 formed by applying energy and growing the metal ions 230. The energy that is applied to form the nanoparticles may be one or more selected from among heat energy, chemical energy, light energy, vibration energy, ion beam energy, electron beam energy, and radiation energy. The diverse embodiments may be the same as or similar to those of the first embodiment of the present disclosure.

In a fabrication method according to a second embodiment of the present disclosure, i) the size of nanoparticles may be controlled by supplying an organic surfactant that is to be bonded to or adsorbed on the metal ions, followed by application of energy. Otherwise, ii) the size of nanoparticles may be controlled during the growth thereof by supplying an organic surfactant that is to be bonded to or adsorbed on the metal ions during application of energy, This supply of the organic surfactant may be optionally performed during the fabrication process. As the organic surfactant that is applied before or during application of energy, one or more kinds of organic surfactants may be used.

To more effectively inhibit the transfer of the metal ions, a first organic material and a second organic material of different kinds may be used as the surfactants.

The first organic material may be a nitrogen- or sulfur-containing organic compound. For example, the sulfur-containing organic material may include a linear or branched hydrocarbon compound having a thiol group at one end. In a specific example, the sulfur-containing organic compound may be one or more selected from a group including $HS-C_n-CH_3$ (n: an integer ranging from 2 to 20), n-dodecyl mercaptan, methyl mercaptan, ethyl mercaptan, butyl mercaptan, ethylhexyl mercaptan, isooctyl mercaptan, tert-dodecyl mercaptan, thioglycolacetic acid, mercaptopropionic acid, mercaptoethanol, mercaptopropanol, mercaptobutanol, mercaptochexanol and octyl thioglycolate.

The second organic material may be a phase-transfer catalyst-based organic compound, for example, quaternary ammonium or a phosphonium salt. More specifically, the second organic surfactant may be one or more selected from a group including tetraocylyammonium bromide, tetraethylammonium, tetra-n-butylammonium bromide, tetramethylammonium chloride, and tetrabutylammonium fluoride.

Figure 2E:
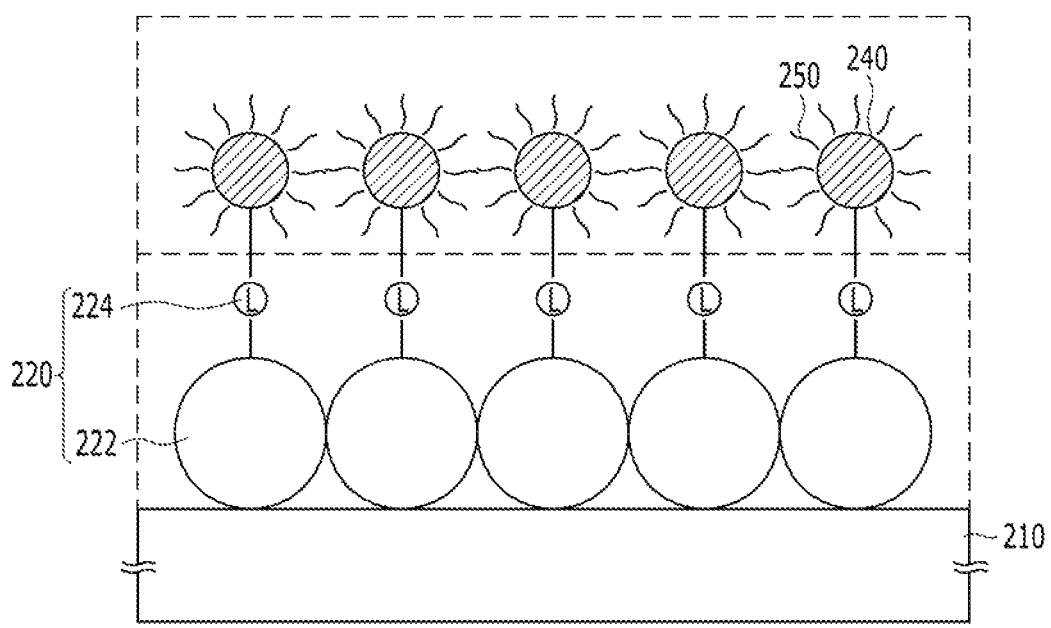

FIG. 2E shows a dielectric organic material 250 bonded to the metallic nanoparticles 240 grown by application of energy. The dielectric organic material 250 may be in a state in which it coats the surface of the metal lie nanoparticles 240 or fills the gaps between the metallic nanoparticles 240. The dielectric organic material 250 may provide isolation between the nanoparticles to more reliably prevent the flow of current between nanoparticles.

If a sufficient amount of the organic surfactant was supplied in the preceding action, that is, if the organic surfactant that is applied before or during application of energy remains on the surface of the grown nanoparticles to provide sufficient isolation between the grown nanoparticles, further dielectric organic material 250 may not need to be added to the surface of the grown nanoparticles 240. In other words, because whether the organic surfactant is to be used or not is determined according to the size of nanoparticles to be formed, step of forming the dielectric organic material 250 after the formation of the nanoparticles 240 is optional.

In the second embodiment of the present disclosure, the method for forming the dielectric organic material 250 and the materials used for the method may be the same as or similar to those of the first embodiment of the present disclosure.

Referring to FIG. 2E, the nano structure formed through the fabrication method in accordance with the second embodiment of the present invention is described in detail.

Referring to FIG. 2E, the nano structure in accordance with the second embodiment of the present invention may include a substrate 210, dielectric particle supporters 222 where the linkers 224 are bonded formed over the substrate 210, and metallic nanoparticles 240 that are grown from metal ions bonded to the linkers 224. Also, the nano structure may further include a dielectric organic material 250 having a functional group bonded to the surface of the metallic nanoparticles 240.

The substrate 210 may include a surface layer 214. The surface layer 214 may include an oxide layer. To be specific, non-limiting examples of the surface layer 214 of the substrate 210 may be a layer of at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, and a hafnium silicate.

The substrate 210 may be a flexible substrate, which may include a surface layer having a hydroxyl (—OH) functional group. The flexible substrate may include one or a mixture of two or more selected from the group including polyethylene terephthalate (PET), polyethylene naphthalate (PEN), polyimide (PI), polycarbonate (PC), polypropylene (PP), triacetyl cellulose (TAC), polyethersulfone (PES), and polydimethylsiloxane (PDMS).

The dielectric particle supporters 222 may be oxide particles including at least one element selected from the group including metals, transition metals, post-transition metals, and metalloids. The dielectric particle supporters 222 may be particles having an average particle diameter of about 10 to 20 nm. The dielectric particle supporters 222 may be formed as a monomolecular layer or a polymolecular layer over the substrate 210.

Also, the dielectric particle supporters 222 may include at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, a hafnium silicate and polymers.

The linkers 224 may be organic monomolecules. The nano structure may include a linker layer formed of the plurality of the linkers 224 bonded to the surface of the substrate 210. The linker layer may be a self-assembled monomolecular layer formed to be self-combined with the surface of the dielectric particle supporters 222. The linkers 224 may include one functional group selected from the group including an amine group, a carboxylic acid group, and a thiol group. The linkers 224 may include first functional groups bonded to the surface of the dielectric particle supporters 222, second functional groups bonded to metal ions, and chain groups for connecting the first functional groups and the second functional groups to each other.

The metallic nanoparticles 240 may be selected from the group including metal nanoparticles, metal oxide nanoparticles, metal nitride nanoparticles, metal carbide nanoparticles, and intermetallic compound nanoparticles. The metallic nanoparticles 240 may be grown by bonding metal ions to the linkers 224 and then growing the metal ions.

The size of the metallic nanoparticles 240 may be controlled according to the energy application conditions while the metallic nanoparticles 240 are grown. Also, the size of nanoparticles may be controlled before the energy for growing the metallic nanoparticles 240 is applied or during energy application by whether a surfactant is supplied. The surfactant may be an organic surfactant, and the surfactant may remain on the surface of the metallic nanoparticles 240 after the growing of the metallic nanoparticles 240 is finished. According to an embodiment of the present disclosure, when no surfactant is used, the metallic nanoparticles 240 may have a particle diameter of about 2.0 to 3.0 nm. According to another embodiment of the present disclosure, when a single kind of surfactant is used, the metallic nanoparticles 240 may have a particle diameter of about 1.3 to 1.6 nm. According to another embodiment of the present disclosure, when a plurality of different kinds of surfactants is used, the metallic nanoparticles 240 may have a particle diameter of about 0.5 to 1.2 nm.

The dielectric organic material 250 may be bonded to the surface of the grown metallic nanoparticles 240. The dielectric organic material 250 may prevent current from flowing through the metallic nanoparticles 240. The surface of the metallic nanoparticles 240 may be coated with the dielectric organic material 250, and the dielectric organic material 250 may fill the space between the metallic nanoparticles 240 that are spaced apart from each other. When a surfactant is supplied to the metal ions, which are the state of the metallic nanoparticles 240 before the metallic nanoparticles 240 are grown, or while the nanoparticles are being grown, the surfactant may remain on the surface of the metallic nanoparticles 240. Since the surfactant may be a dielectric organic material as well, if the arranged nanoparticles are insulative to each other simply by the surfactant remaining after the nanoparticles are grown, further application of dielectric organic material 250 after the nanoparticles are grown may be unnecessary.

Although not illustrated in the drawing, a dielectric material may be additionally formed between the metallic nanoparticles 240 that are coated with the dielectric organic material 250. In other words, in addition to the dielectric organic material 250 being formed, an inorganic oxide material may be additionally formed in order to more stably fix the metallic nanoparticles 240. Also, an inorganic oxide material may be formed directly without the dielectric organic material 250.

The metallic nanoparticles 240 may be spaced apart from each other to form a monomolecular nanoparticle layer. The nanoparticle layer may include a dielectric organic material (or an organic material for a surfactant) bonded to or coating the surface of the metallic nanoparticles 240. The nanoparticle layer may further include an inorganic oxide material that fills the gaps between the coated nanoparticles 240.

The nano structure in accordance with the second embodiment of the present disclosure may have a vertical multi-stack structure. In other words, the nano structure may have a stacked structure where the supporter layer 220, which is bonded to the linkers 224, and the nanoparticle layer are stacked alternately and repeatedly. A dielectric layer having functional groups capable of being bonded to the dielectric particle supporters 222 where the linkers 224 are bonded, may be further included between the lower nanoparticle layer and the upper supporter layer. If the dielectric organic material 250 forming the lower nanoparticle layer has functional groups capable of being bonded to the upper supporter layer, the forming of the additional dielectric layer may be unnecessary. In short, whether to form the dielectric layer may be decided based on the kind of dielectric organic material 250 that is applied.

According to the embodiments of the present invention, the nano structures are extremely fine, have uniform size, and may be fabricated in high density. Also, since the nanoparticles are fixed by dielectric linkers, the nano structures have excellent physical stability. For these reasons, an application device using the nano structures may be easily scaled, and while the application device is scaled, the application device still retains excellent operation stability, reproducibility, and reliability.

According to the embodiments of the present invention, the nano structures may be fabricated through an in-situ process. Therefore, production cost may be minimized, and mass-product ion within a short time may be possible.

The nano structures and fabrication methods thereof in accordance with the embodiments of the present disclosure may have nanoparticle sizes controlled through a simple process of using a surfactant and inducing a reaction during the growth of the nanoparticles. In short, the nanoparticles may be prepared in a desired particle size, while securing the characteristics of an application device.

Although various embodiments have been described for illustrative purposes, it will be apparent to those skilled in the art that various changes and modifications may be made without departing from the spirit and scope of the disclosure as defined in the following claims.

What is claimed is:
1. A nano structure, comprising:
a substrate;
a plurality of dielectric particle supporters formed over the substrate;
a plurality of linkers bonded to the dielectric particle supporters; and
one or more metallic nanoparticles bonded to the linkers.

2. The nano structure of claim 1, wherein the metallic nanoparticles axe grown from metal ions bonded to the linkers.

3. The nano structure of claim 1, wherein each of the dielectric particle supporters includes at least one material selected from the group including a silicon oxide, a hafnium oxide, an aluminum oxide, a zirconium oxide, a barium-titanium composite oxide, an yttrium oxide, a tungsten oxide, a tantalum oxide, a zinc oxide, a titanium oxide, a tin oxide, a barium-zirconium composite oxide, a silicon nitride, a silicon oxynitride, a zirconium silicate, and a hafnium silicate.

4. The nano structure of claim 1, further comprising:
at least one of a dielectric organic material and an inorganic oxide that is bonded to a surface of the metallic nanoparticle.

5. The nano structure of claim 1, wherein the metallic nanoparticle has an average particle diameter of about 2.0 nm to 3.0 nm.

6. The nano structure of claim 1, further comprising an organic surfactant of one or more kinds bonded to the nanoparticle.

7. The nano structure of claim 6, wherein the organic surfactant is a nitrogen-containing organic material or a sulfur-containing organic material.

8. The nano structure of claim 7, wherein the metallic nanoparticle has an average particle diameter of about 1.3 nm to 1.9 nm.

9. The nano structure of claim 6, wherein the organic surfactant includes a first organic material and a second organic material of different kinds, and
the first organic material is a nitrogen-containing organic material or a sulfur-containing organic material, and
the second organic material is a phase-transfer catalyst-based organic material.

10. The nano structure of claim 9, wherein the metallic nanoparticle has an average particle diameter of about 0.5 nm to 1.2 nm.

11. The nano structure of claim 1, wherein the linkers include a plurality of organic monomolecules bonded to surfaces of the dielectric particle supporters.

12. The nano structure of claim 1, wherein the linkers include a plurality of first functional group bonded to the surfaces of the dielectric particle supporters, a plurality of second functional groups bonded to the one or more metallic nanoparticles, and a plurality of chain groups that connect the first functional groups and the second functional groups to each other.

13. The nano structure of claim 2, wherein each of the linkers includes one functional group selected, from the group including an amine group, a carboxyl group and a thiol group as a functional group capable of being bonded to the metal ions.

14. The nano structure of claim 1, wherein the metallic nanoparticle is selected from the group including a metal nanoparticle, a metal oxide nanoparticle, a metal nitride nanoparticle, a metal carbide nanoparticle, and an intermetallic compound nanoparticle.

15. The nano structure of claim 1, wherein the metallic nanoparticles are arranged separately from one another and form a single monomolecular layer.

16. The nano structure of claim 1, wherein the dielectric particle supporters that are bonded to the linker are arranged over the substrate to form a dielectric particle supporter layer.

17. The nano structure of claim 16, further comprising:
a nanoparticle layer formed over the supporter layer, and the nanoparticle layer includes:
a plurality of the metallic nanoparticles spaced apart from each other; and
a dielectric material bonded to a surface of each metallic nanoparticle.

18. The nano structure of claim 17, wherein a plurality of the supporter layers and a plurality of the nanoparticle layers are stacked alternately and repeatedly to form a vertical multi-stack structure.

19. The nano structure of claim 17, wherein the dielectric material includes at least one between a dielectric organic material and an inorganic oxide.

20. A nano structure, comprising:
a substrate;
a plurality of dielectric particle supporters disposed over the substrate;
a plurality of linkers formed on the dielectric particle supporters and suitable for coupling a plurality of metal ions with the dielectric particle supporters; and
one or more metallic nanoparticles formed to the linkers.

21. The nano structure of claim 20, wherein each of the linkers includes one functional group selected from the group including an amine group, a carboxyl group, and a thiol group, as a functional group that is bonded to the metal ions.

22. The nano structure of claim 20, further comprising:
an organic surfactant of one or more kinds bonded to the metal ions or the nanoparticles.

23. The nano structure of claim 20, wherein the metallic nanoparticles have an average diameter of 0.5 nm to 3.0 nm.

24. The nano structure of claim 23, wherein the metallic nanoparticles have a particle radius standard deviation of 20% or less.

* * * * *